(12) United States Patent
Halevy (10) Patent No.: US 6,663,589 B1
(45) Date of Patent: Dec. 16, 2003

(54) CATHETER SYSTEM

(76) Inventor: Haim Halevy, Moshav Manof 52, Misgav (IL), 20184

(*) Notice: Subject to any disclaimer, the term of this patent is extended or adjusted under 35 U.S.C. 154(b) by 34 days.

(21) Appl. No.: 09/597,869

(22) Filed: Jun. 20, 2000

(51) Int. Cl.[7] ............................................. A61M 29/00
(52) U.S. Cl. ........................... 604/96.01; 604/103.06; 604/104; 604/106; 604/523
(58) Field of Search .................. 604/96.01, 103.06, 604/103.07, 103.08, 104, 106, 523

(56) References Cited

U.S. PATENT DOCUMENTS

| | | | |
|---|---|---|---|
| 4,445,892 A | 5/1984 | Hussein et al. | |
| 4,909,252 A | * 3/1990 | Goldberger | 604/103.1 |
| 4,927,412 A | 5/1990 | Menasche | |
| 5,152,772 A | 10/1992 | Sewell, Jr. | |
| 5,195,970 A | * 3/1993 | Gahara | 604/103.08 |
| 5,211,631 A | * 5/1993 | Sheaff | 604/103.05 |
| 5,308,325 A | 5/1994 | Quinn et al. | |
| 5,370,653 A | 12/1994 | Cragg | |
| 5,480,644 A | 1/1996 | Freed | |
| 5,490,984 A | 2/1996 | Freed | |
| 5,531,712 A | 7/1996 | Malcolm | |
| 5,620,418 A | 4/1997 | O'neill et al. | |
| 5,628,786 A | 5/1997 | Banas | |
| 5,653,690 A | 8/1997 | Booth | |
| 5,720,726 A | 2/1998 | Marcadis | |
| 5,800,478 A | 9/1998 | Chen | |
| 5,800,520 A | 9/1998 | Fogarty | |
| 5,891,154 A | * 4/1999 | Loeffler | 606/194 |
| 5,895,400 A | 4/1999 | Abela | |
| 5,899,850 A | 5/1999 | Ouchi | |
| 5,980,483 A | 11/1999 | Dimitri | |
| 5,993,484 A | 11/1999 | Shmulewitz | |
| 6,045,570 A | 4/2000 | Epstein | |
| 6,152,943 A | 11/2000 | Sawhney | |
| 6,159,197 A | 12/2000 | Heuster | |
| 6,200,256 B1 | 3/2001 | Weinberger | |

FOREIGN PATENT DOCUMENTS

EP  0 750 919 A2  1/1997

* cited by examiner

*Primary Examiner*—Thomas Denion
*Assistant Examiner*—Theresa Trieu
(74) *Attorney, Agent, or Firm*—Edward Langer; Shiboleth, Yisraeli, Roberts, Zisman & Co.

(57) ABSTRACT

A catheter according to the present invention comprises
- a tube having a distal end and an open proximal end;
- at least one fluid conduit disposed within and along the tube, the fluid conduit having open proximal end and a closed distal end;
- an expandable balloon in fluid communication with the at least one fluid conduit; and
- anchoring means for securely engaging the catheter in a passage, the anchoring means being located on a surface of the balloon and operable by the expansion of the balloon.

13 Claims, 8 Drawing Sheets

CATHETER SYSTEM

FIELD OF THE INVENTION

The present invention relates to improved catheters and to kits comprising them, and, in particular, to catheters securable to bodily tissues, used in the diagnostics and in the treatment of fistulae, sinuses and the like, and to kits comprising them.

BACKGROUND OF THE INVENTION

A catheter is a medical device, shaped as a generally elongated tubular member and made to be pushed into and inserted through a bodily cavity, lumen, fistula, sinus, blood vessel or other passage. A fistulae is a pathological bodily passage whose contour or path within the body is usually irregular and not known in advance. It is to be understood that a general term used hereinbelow for bodily cavities, lumens, fistulae, sinuses, blood vessels and other bodily passages, is passage. It is further understood that all passages comprise an inner surface.

Catheters comprise at least one fluid conduit along at least part of their lengths. Catheters of numerous designs, serving different medical uses, are known in the art. A common use of many types of catheters is the draining of bodily fluids from a patient's body cavity, by conducting them through a fluid conduit disposed within the catheter and rejecting them outside of the patient's body. However, many other catheter types, intended for numerous and different uses, are known.

Catheters incorporating inflatable and expandable member or members, usually called balloons, are known. Well known among them, and incorporating features found in many such devices, is "Foley catheter" whose mode of operation is described hereinbelow. Foley catheter are designed to be inserted into the urinary tract and to drain and reject the urine outside of the patient's body. Foley's catheter comprises an elongated tube having a distal end and a proximal end, a working section extending distally from the proximal end and two internal, generally parallel fluid conduits in fluid isolation between themselves and disposed along the inner side of said tube. One fluid conduit is an inflating conduit and is in fluid communication between an expandable balloon extending from the distal end of the catheter's tube and an inflating port positioned in the working section of the catheter. The other conduit is a drainage conduit and is in fluid communication between a drainage port located in the working section of the catheter and the outer surface of the catheter's tube via one or more orifices passing between the wall of said tube and the drainage conduit, said orifices are disposed along the tube and proximally away from said balloon. This catheter is passed through the urinary tract and into the bladder, whose diameter is much larger than that of the urinary tract. Then the balloon is inflated and expanded via the inflating port and the inflating conduit to a sufficiently large diameter. The expanded balloon abuts the bladder and anchors the catheter in place by preventing its dislodging through the urinary tract and outside of the patient's body. Then the urine flows through the orifices, into the drainage conduit and to the drainage port, from which the urine is discharged out of the patient's body.

Other catheters are shown in many US and other patents. For example, U.S. Pat. No. 4,445,892 discloses a catheter device that functions as an endoscope, provided with two spaced apart and expandable balloons used in the endoscopic visualization of a length of a blood vessel between said two balloons. U.S. Pat. No. 5,898,850 discloses a treatment accessory serving as a sheath and a guide for a cytology brush used for the removal of samples from a passage. U.S. Pat. No. 5,152,772 describes a catheter carrying two spaced apart expandable balloon and a retractable blade disposed therebetween. U.S. Pat. No. 5,895,400 discloses a sweeping brush carried within a catheter and used in the removal of material such as thrombus from arteries. Numerous other U.S. Patents disclose catheters that teach the use for many other highly varied purposes.

Catheters are often made of soft materials, such as latex When the passage into which the catheter is pushed and inserted is not straight, a soft catheter might collapse and fold if pushed hard enough. A collapsed or folded catheter no longer advances through the passage. The catheter material is sometimes stiffened either by using stiffer materials or by the insertion of stiffeners into the soft matrix of the catheter, thus lowering the chance of a catheter collapse or folding. On the other hand, too stiff catheters might penetrate through the passage walls and injure the healthy tissue. The determination of the preferred catheter stiffness for a particular passage contour and length depends largely on the surgeon's experience and judgement.

In order to overcome this difficulty, a guide wire is often used. A guide wire is a wire whose diameter is smaller than that of the conduit inner diameter of the catheter so that it could pass through the catheter. Guide wires are made of a fairly stiff material such as hard plastic material or metal, permitting the guide wire to transmit relatively large compressive forces in the general direction of the guide wire axis. When inserted into a catheter, the guide wire stiffens it and permits the pushing of the catheter into a passage with a lower risk of catheter folding or collapse. There exists a variety of guide wires made of different materials and having different diameters, offering their users a choice of a wide range of stiffnesses, Catheters made to utilize guide wires often include a special small diameter, inner tubule disposed within their main tube for containing the guide wire, said tubule is usually in fluid isolation from any other conduit. Sometimes a guide wire is first inserted into the passage, bent and shaped to follow the passage contour and then a catheter is pushed into the passage while sliding along the guide wire. In other cases, a first catheter is first passed through the passage, a guide wire to be used by a second catheter is then inserted into the first catheter and pushed through it, thus the guide wire is shaped according to the passage contour, the first catheter is then extracted off the patient's body while leaving the shaped guide wire in place, and a second catheter is pushed along the guide wire. Other methods of using guide wires are known.

SUMMARY OF THE INVENTION

Catheters are elongated tubular members, insertable into passages, often used for the introduction of medical preparations into particular body parts. Their proper sealing capability, for preventing medical preparations from reaching undesirable body parts, is of utmost importance for proper medical treatment, as is their secure positioning.

According to the present invention there is provided an improved catheter capable of providing improved sealing along passages, as well as a secure and selectable engagement to passages at desired locations along said passages. The present invention further provides for catheters especially adapted for the treatment of fistulae by aiding in the determination of the contours of fistulae and in dispensing medical drugs and other medical preparations for their diagnostics and treatment. The present invention still further provides for kits containing catheters according to the present invention and other medical supplies required during the use of said catheters.

Also according to the present invention, a catheter is provided with an outwardly expandable balloon extensible from the catheter's circumference wherein the external surface of said balloon actuates means providing for improved sealing and high frictional forces between said expanded balloon and the passage into which it is inserted. This improved sealing divides said passages into a proximal section and a distal section, separated by said balloon, and isolates one section of the passage from the other, lowering the likelihood that material dispensed in one section of the passage might flow across the balloon to its other section, thus preventing backflow. This isolation is important during the dispensation and the application of drugs, contrast madia, tissue sealants and the like along said passages or into cavities joining them, or for draining said passages and cavities.

Additionally, the high frictional forces secure and anchor the catheter to the patient's body and prevent the catheter's inadvertent dislodging. Thus, any medical activity could be performed without fear of dislodgement of the catheter or of undesireable fluid flow along the passage. If desired, the balloon could then be deflated and the catheter be moved to another location within the passage, or the catheter could be taken out of the patient's body. This novel feature of the invented catheters permits the long term securing of catheters to a passage, thus often eliminating the need for sutures.

According to one embodiment of the present invention, said outwardly expandable balloon extensible from the catheter's circumference is provided with a radially and externally protruding circumferential rib near the balloon's largest expanded radius and surrounding it, so as to provide for good sealing and high frictional forces between said expanded balloon and the passage into which it is inserted.

According to another embodiment of the present invention, said catheter is provided with a balloon and with a plurality of elongated, relatively stiff, circumferentially disposed, axially oriented, rods, wherein one end of said rods being attached to the catheter outer surface away from said balloon and the other end of said rods rests on said balloon, said rods pointing in the general direction of the catheter axis while said balloon is fully deflated. Flexible webs extend between said rods, forming a shell. When said balloon is expanded while at any selected position within a passage, said rods are pushed against and into the inner surface and the tissue of said passage, therefore anchoring the catheter to said passage at a selected position. During the balloon's expansion said webs expand to form a generally conical shell, sealing said passage for flow through said shell and along said balloon.

According to yet another embodiment of the present invention, the external surface of said balloon is roughened so as to provide for improved sealing and higher frictional forces between said expanded balloon and the passage into which it is inserted, improving the sealing in the contact area between the balloon and the passage inner surface, and securing and anchoring the catheter to the patient's body.

Fistulae are pathologically created passages whose contour or path within the body is usually irregular, and are among the most likely passages to be treated by the catheter of this invention. Fistulae tend to suppurate or to be filled by bodily fluids and other materials, causing infections which are difficult to heal. Currently, many fistulae are removed by surgical intervention. The surgical treatment calls for a knowledge of the fistula's path because some of the fistulae paths pass too close to body parts or organs that may not be operated on or might be harmed during a fistula operation. Currently, a fistula path can usually be determined only by surgery: Only at that stage can the surgeon determine whether or not the fistula's repair is possible and proceed with the operation.

It is also a purpose of the present invention to provide catheter for the opening of fully or partially blocked passages by inserting, securing and expanding the catheter's balloon near the blocked area. A blocked bodily passage may be opened by injecting into said passage, under sufficiently strong pressure, an injectable material. The injectable material could by oil, vaseline or other suitable material and it could also serve other functions such as a lubricant. Alternatively, or in addition to injection, the catheter's balloon may open blocked passages or sections thereof during its expansion. Once a blocked area is opened, the catheter can be further inserted and the opening procedure be repeated as necessary. When the passage's contour is cleared and the catheter is fully inserted as is necessary, a contrast media for x-ray or for other imaging methods is inserted through the catheter into and along the passage, permitting the elucidation of the shape and of the location of the passage by non surgical methods. It is to be understood that media is used hereinbelow as a general term for x-ray contrast media, for contrast enhancing material used by other methods, as well as for dye and for lubricant.

It is another purpose of the present invention to provide catheter used for the debriding of the inner surface of a passage in order to permit its subsequent treatment by the application of medical preparations.

It is yet another purpose of the present invention to provide another catheter for the application of drugs used in the treatment and healing of the inner surfaces of a preferably debrided fistulae.

It is still yet another purpose of the present invention to provide kits containing catheters according to the present invention and other medical items likely to be used during the same treatment with said catheters. The above and other features of the present invention will be more readily understood when the following detailed description is considered in conjunction with the accompanying drawings

BRIEF DESCRIPTION OF THE DRAWINGS

The present invention will be better understood and appreciated from the following detailed description taken in conjunction with the drawings in which.

DETAILED DESCRIPTION OF THE INVENTION

The present invention relates to improved catheters capable of being selectably and temporarily engaged in selected positions along the passages into which they are inserted, each catheter capable of establishing a fluid sealing area between itself and said passage, thus preventing a fluid flow between parts of said passage separated by said sealing area, as well as being secured in place and preventing their inadvertent extraction from the patient's body.

In particular, the present invention relates to catheters adapted for use in one or more stages of treatment of fistulae, as shown hereinunder:

for aiding in the determination of the shapes and paths of passages, and especially of fistulae, by facilitating the dispensing of media used in imaging method along fistulae and other passages.

for aiding in the debriding of fistulae by providing means for inserting guide wires along fistulae and other passages for guiding debriding brushes therealong;

for aiding in the drainage over a long time period, on the order of days and weeks, of infected fistulae and other passages; and for dispensing healing factors and/or drugs for the medical treatment of fistulae and other passages.

Figure 1:
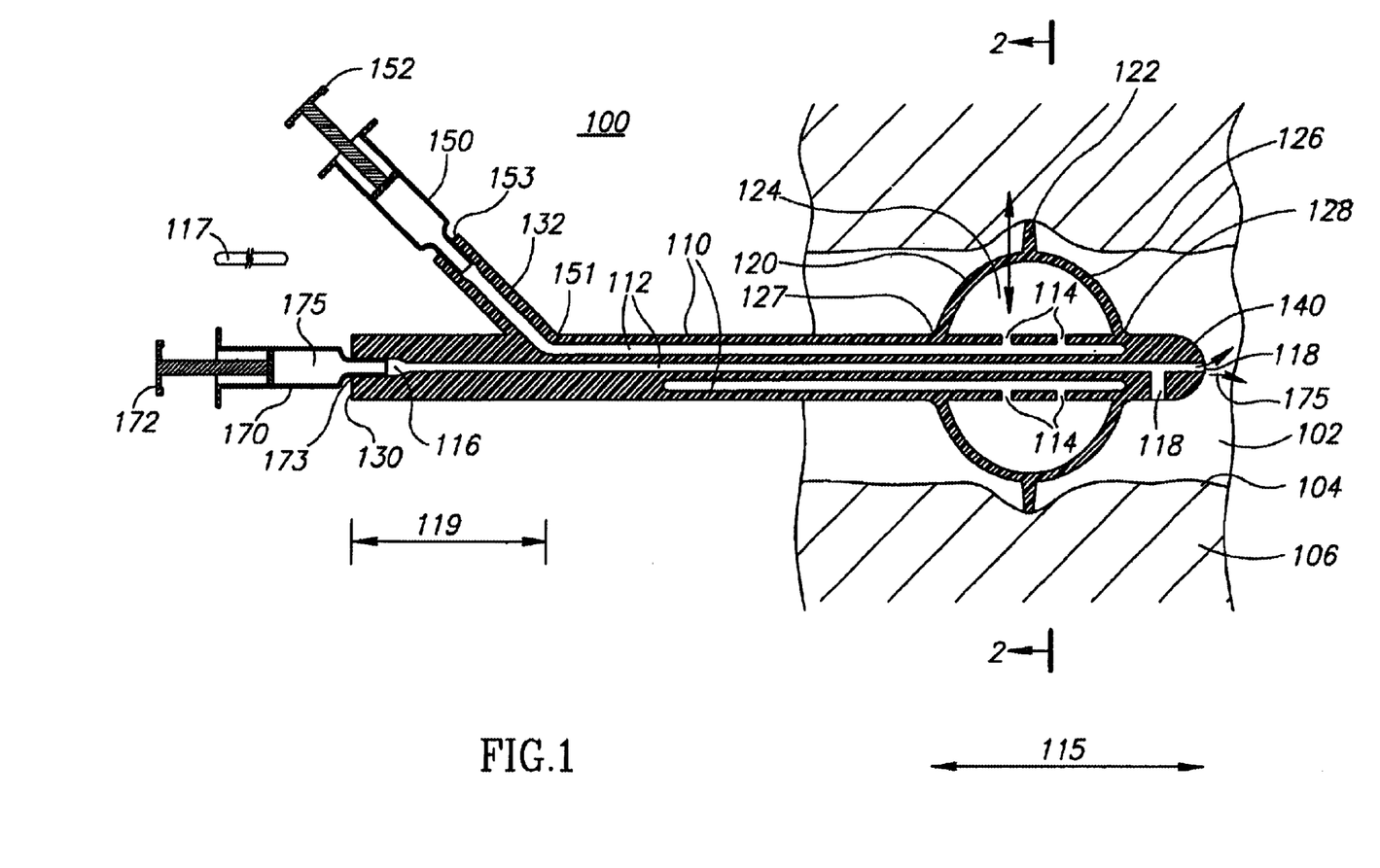
FIG. 1 is a side view, partly in section, of a catheter provided with engaging means according to this invention.

Turning now to FIG. 1 of a preferred embodiment of catheter 100 permitting the non surgical visualization of a fistula's contour within a patient's body and disposed with anchoring, deblocking, sealing and visualizing means of a passage 102 such as a fistula according to the present invention. A fistula is a pathological passage whose contour or path within the body is not usually known in advance, and which is often full with decaying matter. The determination of the fistula's contour is most often done during the course of a surgery, and after its determination it is frequently found that the fistula cannot be surgically removed as it passes too close to some internal organ, therefore the operation must be stopped.

Figure 2:
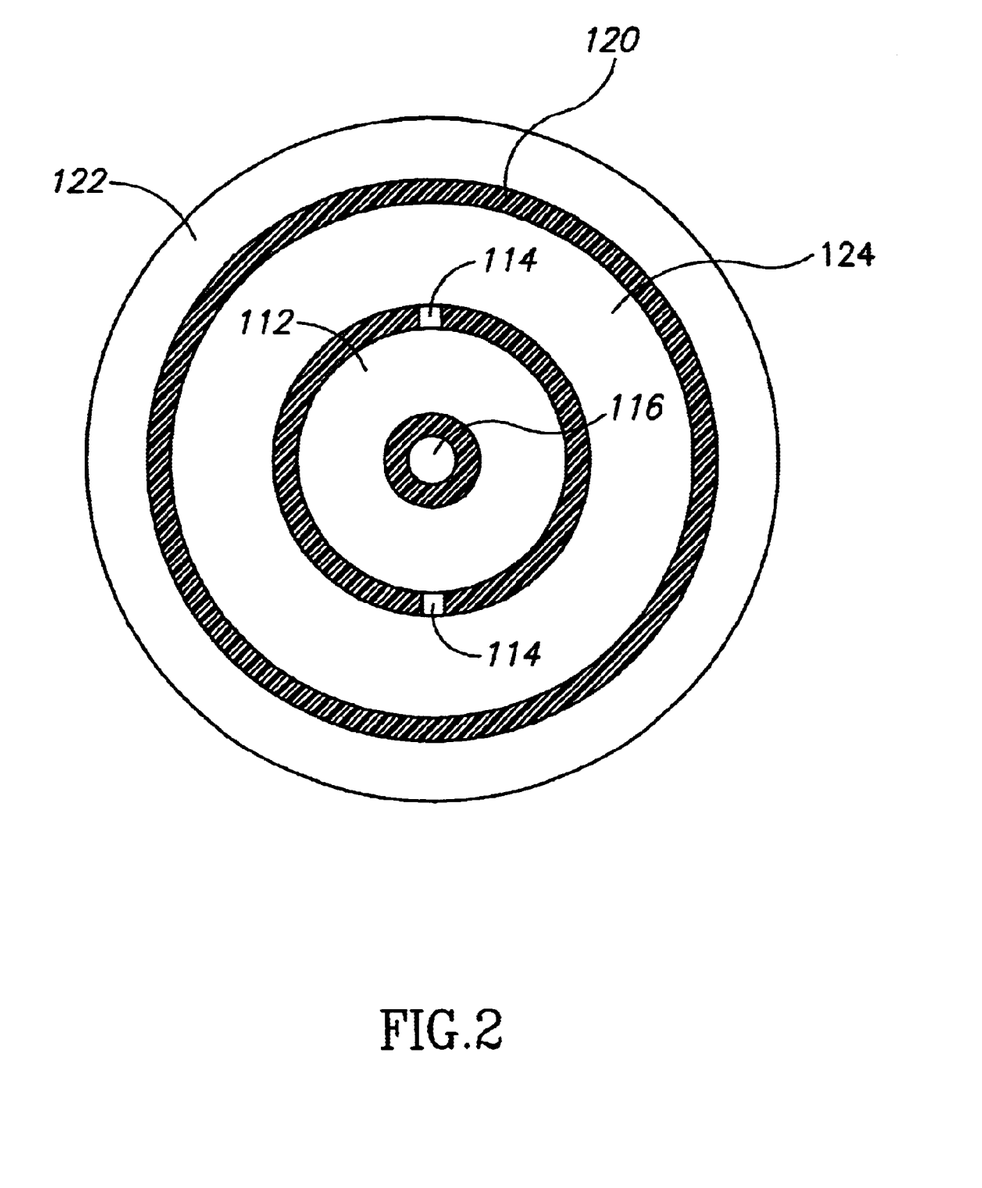
FIG. 2 is a section through the catheter shown in FIG. 1 according to this invention.

The preferred embodiment shown in FIG. 1 depicts a catheter for a non-surgical elucidation of the contour of a passage such as fistula. The catheter is inserted and secured by expanding it inside the passage inner diameter and, if necessary, unblocking the passage by either expanding, deflating and advancing the catheter through the passage, or by injecting under pressure through the catheter and into the passage an injectable material, such as oil or some other lubricant. Then there is injected into and along the passage a material creating contrast in an X-ray image or similar, thus permitting a non-surgical determination of the passage's contour prior to an operation. The catheter of FIG. 1 further permits the insertion of a guide wire into catheter 100 either in order to stiffen the catheter or in order to leave the guide wire within passage 102 for subsequent use. This is done without injuring the passage, as shown hereinunder. Catheter means 100 is inserted into a passage 102 having inner surface 104 and passing through tissue 106. Catheter means 100 comprises a tube 110, tube 110 having open, proximal and distal ends 130 and 140, respectively. A tube 132 having port 153, branches off tube 110, near proximal end 130 and distally away from it. Tube 132 is in fluid communication with fluid conduit 112. An inflatable, outwardly expandable and inwardly contractable balloon 120 is disposed proximally away from said distal end, said balloon having a proximal side 127 and a distal side 128. The catheter section between the distal end 140 and including the proximal side 127 of balloon 120 forms the distal section 115 of said catheter means. Balloon 120 is provided with a radially and externally protruding circumferential rib 122 surrounding balloon 120, preferably near the largest expanded radius of balloon 120, so as to provide for good sealing and high frictional forces between balloon 120 and passage 102 into which it is inserted. Port 153, serving as an inflating port, is in fluid communication with fluid conduit 112, disposed within tube 110 and serving as an inflating conduit. Inflating conduit 112 is also in fluid communication with a through orifice 114, said orifice establishing fluid communication between fluid conduit 112 and inner volume 124 of balloon 120. Inflating means, such as first syringe 150 and its plunger 152, is in fluid communication with inflating port 153 such as by being snugly inserted into it.

Another inflating means, such as second syringe 170 and its plunger 172, is in fluid communication with proximal end 130, serving also as an injection port. Inflating port 153 has a point 151 located most distally along tube 110. The catheter section extending between proximal end 130 and including both point 151 as well as inflating port 153 and injection port 173, is the work section 119. By pushing plunger 152 towards said inflating port, air or other fluid is forced into inner volume 124, inflating balloon 120. By pulling plunger 152 away from said inflation port air or other fluid previously forced into inner volume 124 of said balloon flows out of balloon 120, deflating and contracting it. Rib 122 is forced against inner surface 104 of passage 102 by expanded balloon 120 and engages balloon 120 and catheter means 100 to tissue 106, therefore anchoring catheter means 100 a selectable location along passage 102. Other suitable securing and anchoring means, such as the means shown in FIG. 2, could also be used to secure the catheter to passage 102. Inflated balloon 120 pushes rib 122 against the inner surface 104 of passage 102, and exerts force on inner surface 104 of passage 102, establishing good sealing between balloon 120 and passage 102, preventing any flow past rib 122. Inflating balloon 120 also helps to open any blocked, or partly blocked sections of passage 102 near balloon 120. When balloon 120 is deflated and contracted, catheter means 100 disengage and permits further insertion of catheter means 100, sealing another part of passage 102, opening, if necessary, any other blocked part of passage 102 or pulling catheter 100 out of the passage 102. Injection port 130 is in fluid communication with fluid conduit 116. Conduit 116 is in fluid isolation from conduit 112 and is in fluid communication with at least one injection orifice 118, disposed along tube 110 between the distal end 128 of balloon 120 and the distal end 140 of tube 110, each orifice 118 establishing fluid communication between the inner and the outer sides of tube 110. After a full insertion of catheter 100 along the desired length, an injectable material 175 capable of creating contrast in x-ray images, or in some other internal image forming means, is injected via port 173, through conduit 116 and orifice 118 into said passage 102. Injectable material 175 contains lubricants assisting the insertion of catheters and dyes useful in the detection of its leaks such as along balloon 120. Catheter means 100 is gradually retracted while more media 175 is injected along the contour of passage 102, thereby leaving a contrast trail. An x-ray image, or any image taken by other appropriate means, such as fistulography, is taken, permitting the surgeon to decide upon further steps.

A guide wire 117 can be inserted into and passed through conduit 116 for stiffening catheter 100. Catheter 100 and guide wire 117 may be bent to fit an assumed contour of passage 102 before the insertion of catheter 100 into the passage 102, and may be inserted into conduit 116 either before the insertion of catheter 100 into passage 102 or during any other subsequent step.

After injecting media 175, catheter 100 is extracted off the patient's body. Guide wire 117 may be left within passage 102, permitting the implementation of the next stages of the treatment.

Usually, the inner part 104 of passage 102 has to be debrided, namely decaying tissues and debris have to be removed, in order to permit the application of biological sealing or irritant material or other granulation promoter or fibrosis activator, that heals and closes the passage.

Turning to FIG. 2, there is shown a cross section of catheter means 100, tube 110, conduits 112 and 116, as well as inflated balloon 120 with rib 122 and inner volume 124.

Figure 3:
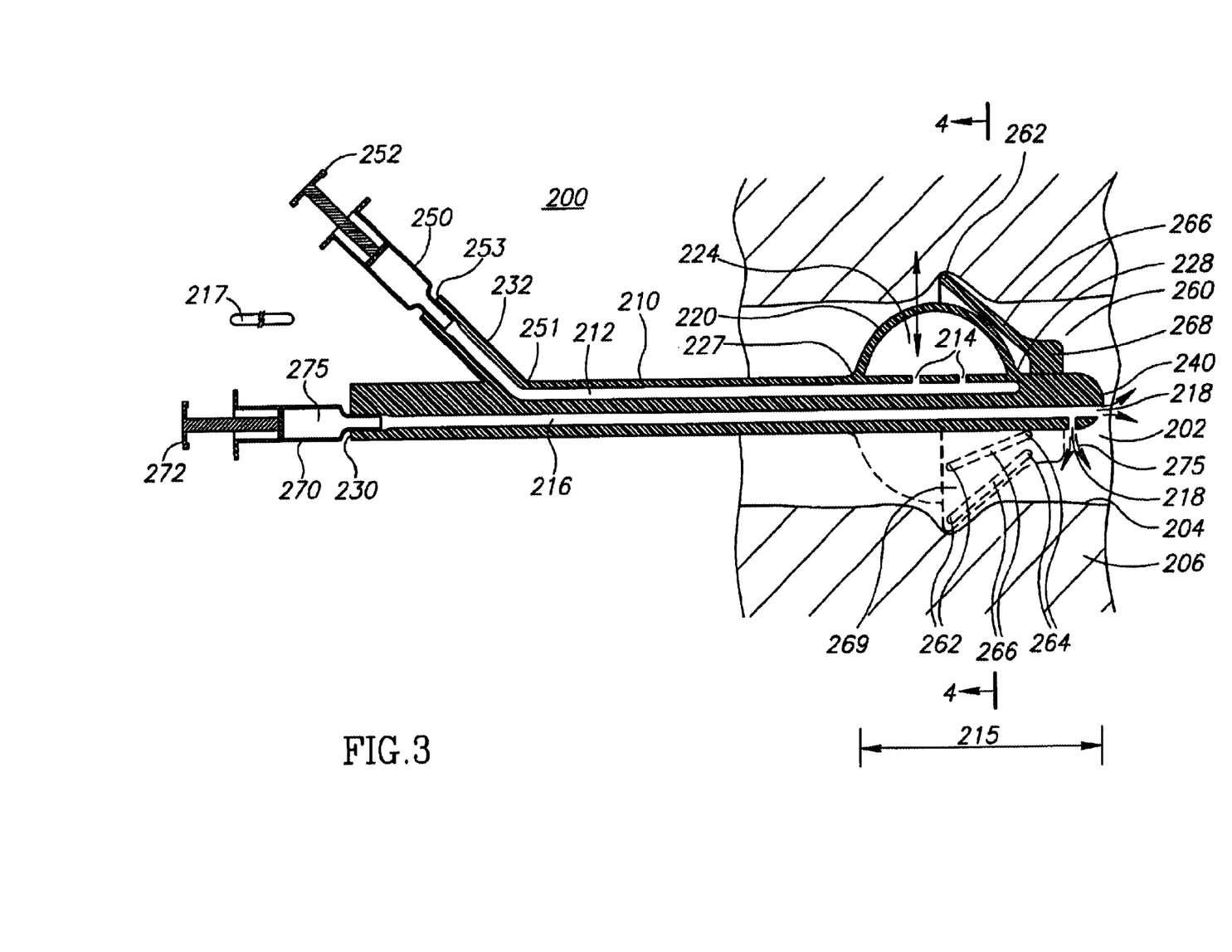
FIG. 3 is a section view of another catheter provided with different engaging means according to this invention.

The catheter means 200 shown in FIG. 3 is similar to the catheter means 100 of FIG. 1. The main difference is in the location of the injection orifices: in FIG. 1 injection orifices 118 are disposed distally away from balloon 120. In FIG. 3, injection orifices 218 are disposed proximally away from balloon 220.

Turning to FIG. 3, there is shown a preferred embodiment of a catheter means 200 disposed with anchoring means to a passage or cavity 202 such as a fistula according to the present invention. Catheter means 200 is made to be inserted into a passage 202, passing through tissue 206 and having inner surface 204. Catheter means 200 comprises a tube 210, tube 210 having an open proximal end 230 and a distal end 240. Tube 232 having an inflating port 253, branches off tube 210, near proximal end 230 and distally away from it. Tube 232 is in fluid communication with fluid conduit 212, passages 214 and inner volume 224 of an inflatable, expandable and contractable balloon 220, disposed proximally away from distal end 240, said balloon having a proximal end 227 and a distal end 228. Catheter means 200 also comprises inner tubular conduit 216, in fluid isolation with conduit 212, tubular conduit 216 being made to pass guide wire 217 and to serve as a fluid conduit. Guide wire 217 may be inserted into fluid conduit 216 either before the insertion of catheter 200 into passage 202, during catheter 200 insertion or after completion of the insertion and before the withdrawal of catheter 200 out of passage 202. Catheter 200 and guide wire 217 may be bent to fit an assumed contour of passage 202 before the insertion of catheter 200 into the passage 202.

Tube 210 carries on its outer surface a ring assembly 260, made of a flexible material, comprising ring 268 from which project several rods 266, connected to said ring at their base ends 264 and having rod tips 262. Flexible webs 269 extend between ring 268 and rod tips 262 and are connected to rods 266 along their lengths to form a continuous membrane. Rods 286 are forced against inner surface 204 of passage 202 by expanded balloon 220 and engage balloon 220 and catheter means 200 to tissue 206, therefore anchoring catheter means 200 at a selectable location along passage 202. Other suitable securing and anchoring means, such as the means shown in FIG. 1, could also be used to secure the catheter to passage 202. When balloon 220 is deflated and contracted, catheter means 200 disengages and permits further insertion of catheter means, or its pulling out of passage 202. Inflating balloon 220 and inserting rods 266 into passage 202 also expands web 269 and establishes a seal between both sides of web 269, preventing fluid flow between the proximal and the distel ends of catheter 200.

The catheter section between the distal end 240 and including proximal end 227 of balloon 220 forms the distal section 215 of said catheter means. Inflating means, such as syringe 250 and its plunger 252 is in fluid communication with inflating port 253 such as by being snugly inserted into it. An injecting means, such as syringe 270 and its plunger 272 is in fluid communication with injection port 230. Inflating port 253 has a point 261 located most distally along tube 210. The catheter section extending between proximal end 230, including point 251 as well as inflating port 253 and injection port 273, is the working section 219. By pushing plunger 252 towards inflating port 253, air or other fluid is forced into inner volume 224, inflating balloon 220. By pulling plunger 252 away from said inflation port air or other fluid previously forced into is inner volume 224 of said balloon flows out of balloon 220, deflating and contracting it.

Inflating balloon 220 exerts force on the inner surface 204 of passage 202 end opens any blocked, or partly blocked passage sections near the balloon. When balloon 220 is deflated and contracted, catheter means 200 disengage and permits further insertion of catheter means, opening, if necessary, any blocked part of passage 202 or pulling catheter 200 out of the passage 202. Injection port 230 is in fluid communication with fluid conduit 216; conduit 216 being in fluid isolation from conduit 212. Conduit 216 is in fluid communication with at least one injection orifice 218, disposed along tube 210 proximally away from balloon 220, each orifice 218 being in fluid communication with the outer side of tube 210. After full insertion of catheter 200 along the desired length, a fluid or paste-like material 275 serving as sealant or granulation stimulant, fibrosis activator or clotting activator factors is injected via port 230, through conduit 216 and at least one orifice 218 into said passage 202. Injected material 275 glues or stimulates the healing of the cleaned, debrided surface 202. Material 275 should not reach any body cavities located beyond passage 202. This necessitates good sealing to be provided by flexible webs 269 and the inner surface 204 of passage 202, and requiring the proximal location, relative to balloon 220, of orifices 218. Catheter means 200 is gradually extracted while more material 275 is injected along the contour of passage 202.

After injecting material 275, catheter 200 and guide wire 217 are extracted off the patient's body. Catheter 200 may also be made of a bloabsoluble material, such as the commercially available Dexon (tm), thus eliminating the need for its extraction from the passage.

Figure 4:
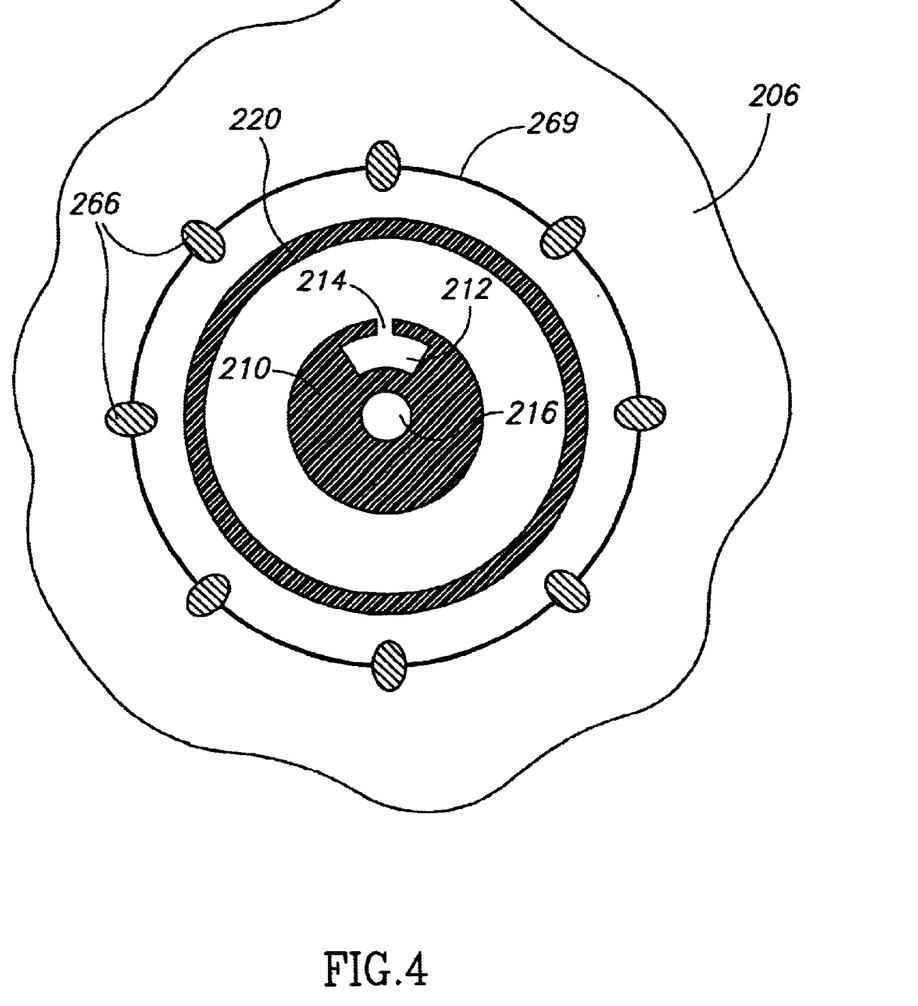
FIG. 4 is a section through the catheter shown in FIG. 3 according to this invention.

Turning to FIG. 4, a cross section of catheter means 200, tube 210, conduit 212 and conduit 216 are shown, as well as conduit 214 and inflated balloon 220 with inner volume 224, rods 266 and webs 269, anchored to tissue 206.

Figure 5:
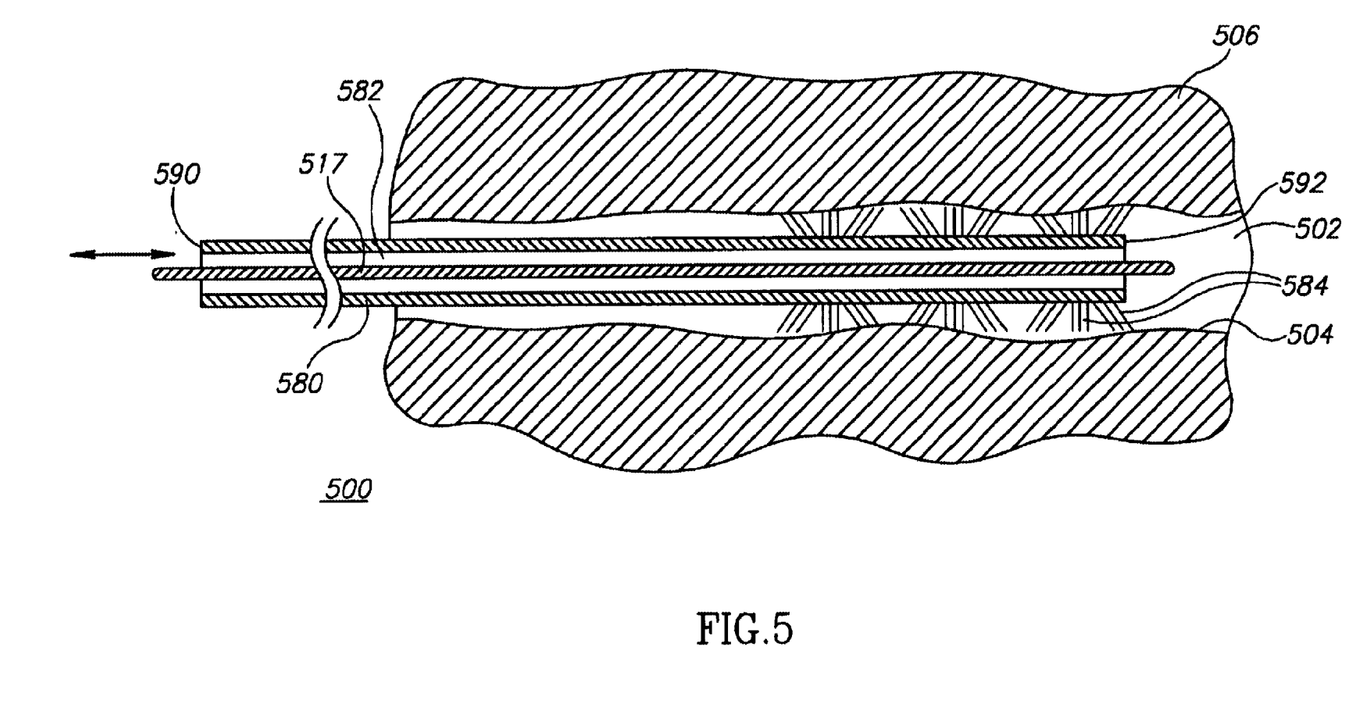
FIG. 5 is a section through a debriding brush according to this invention.

Turning now to FIG. 5, in which a preferred embodiment of debriding brush according to the present invention is shown. Brush 500 comprises a tubular stem 580 having a proximal end 690 and a distal end 592 and an inner passage 582. Brush 500 is made to slide along guide wire 517, previously inserted into passage 502. Guide wire 517 is inserted as is guide wire 117, shown in FIG. 1 hereinabove, at an earlier stage of the treatment, and is inserted into passage 502 formed within tissue 506 and forming inner surface 604. Brush 500 may also be inserted into passage 502 before the insertion of guide wire 517 into brush 500, or guide wire 617 might be inserted into brush 500 and then both brush 500 with guide wire 517 inserted in it, could be inserted into passage 502. Brush 500 also comprises bristles 584 disposed circumferentially around stem 580 near distal end 592 and proximally away from it, along part of the length of stem 580. Debriding is done by moving brush 500 relative to passage 502, such as by sliding or rotating, therefore removing the debris (not shown) from inner surface 504 of passage 502. Brushes could be replaced during the debriding process and different brushes, possibly having different properties, may be used.

Figure 6:
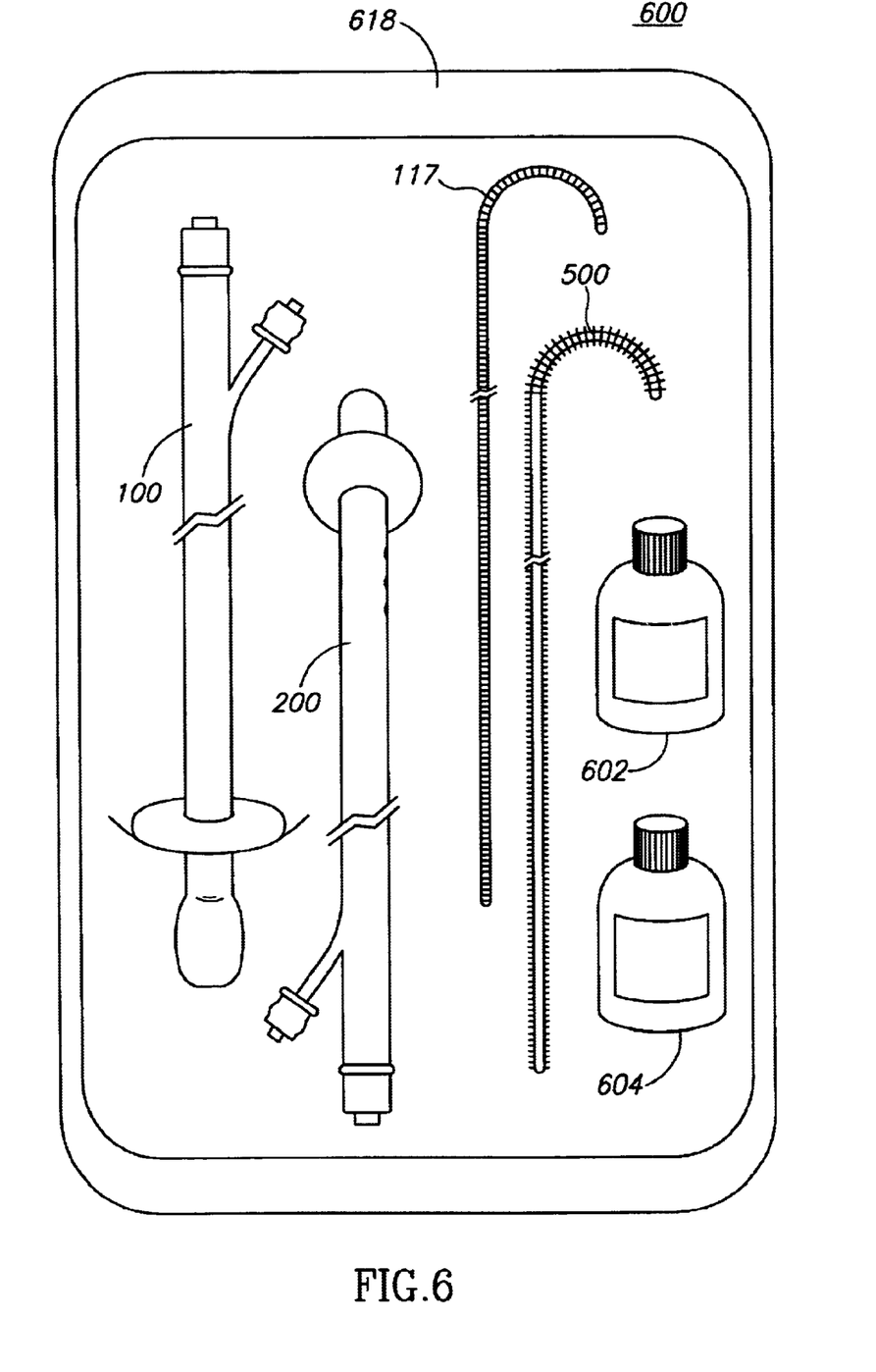
FIG. 6 is a plan view of a kit containing catheters according to this invention and other related surgical and medical supplies.
Figure 7:
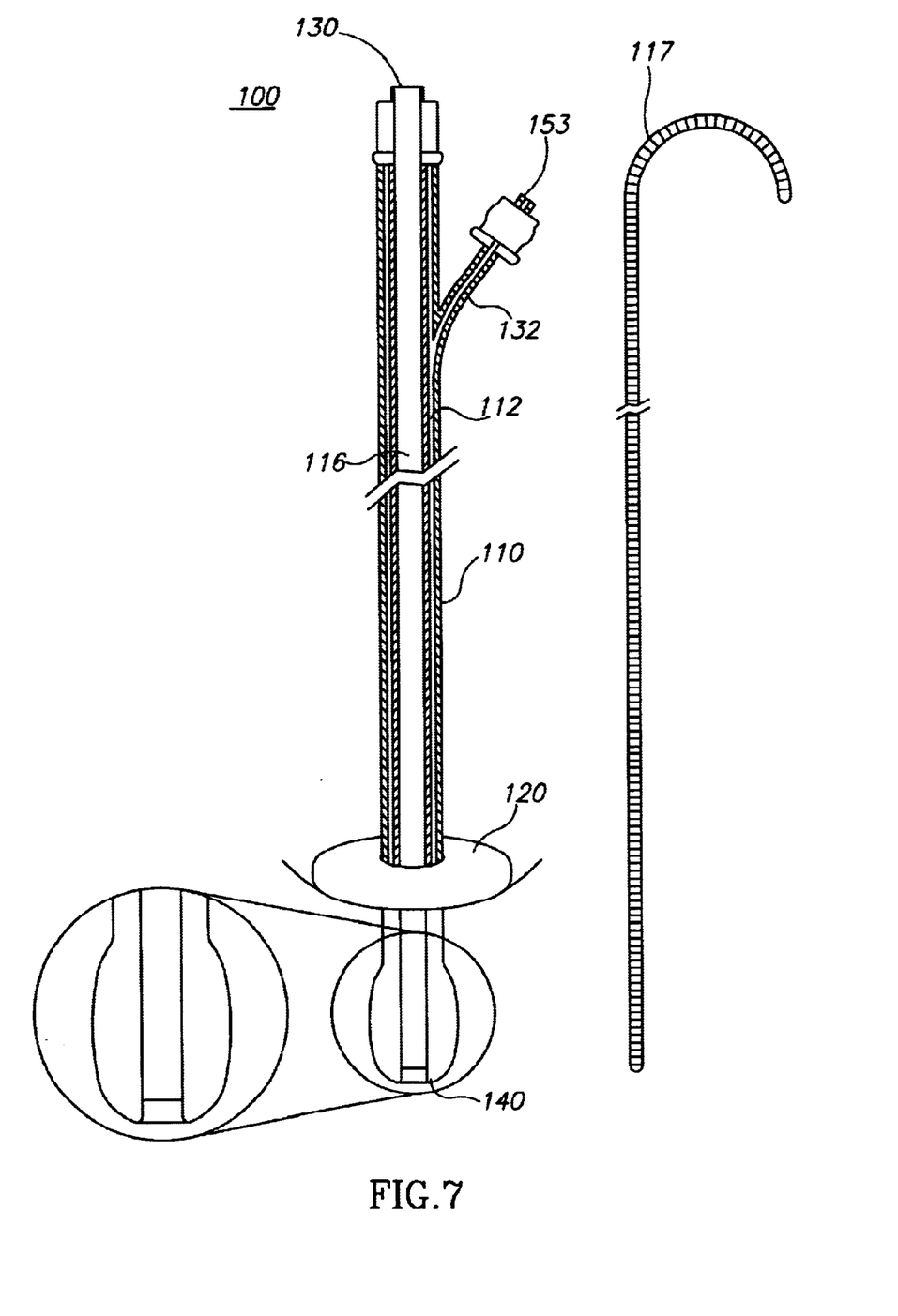
FIG. 7 is an elevational view, in partial cross-section, with a portion shown in detail, of a variation of the catheter shown in FIG. 1 hereinabove, together with a guide wire.
Figure 8:
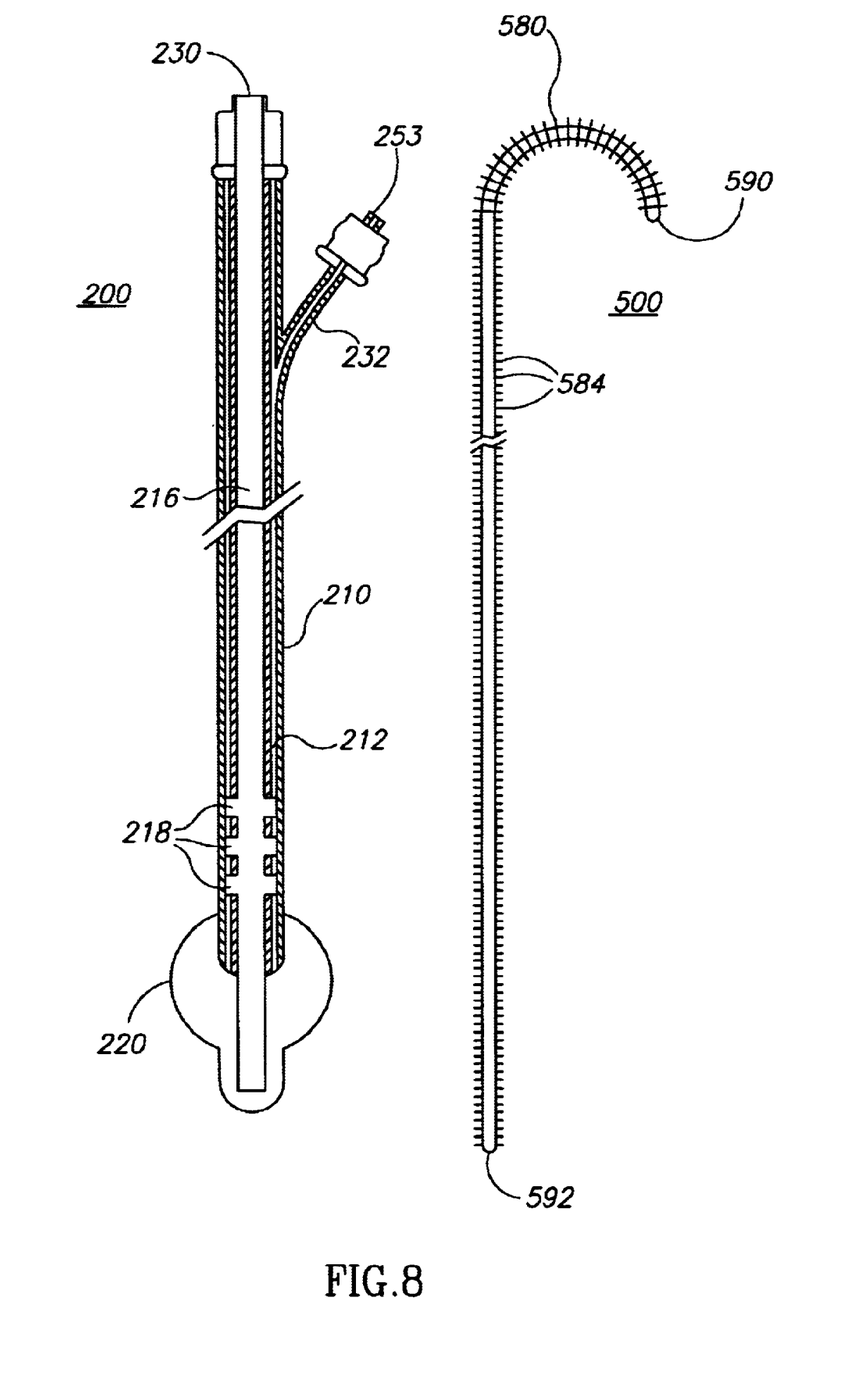
FIG. 8 is an elevational view, in partial cross-section, with a portion shown in detail, of a variation of the catheter shown in FIG. 3 hereinabove, together with a debriding brush.

Turning to FIG. 6 of a preferred embodiment of a kit 600 including catheters 100 and 200, and may include other surgical supplies such as debriding brush 500 or several guide wires 617 having different rigidities, and bottles of fibrin sealant 602 and colored luricant liquid 604 packed in container 818.

It should be understood that the above-shown embodiments are for illustrative purposes only. Various modifications and adaptations will be apparent to those skilled in the art and it will be appreciated that the scope of the present invention should be determined only in reference to the claims appended hereto.

I claim:

1. A catheter for use in treatment of fistulae by introduction of an injectable fluid, the catheter comprising:
   a tube having a distal end and an open proximal end;
   a first fluid conduit disposed within and along said tube, said fluid conduit having open proximal end and a closed distal end;
   a first syringe in fluid communication with said first fluid conduit;
   an expandable and contractable balloon in fluid communication with said first fluid conduit;
   a second fluid conduit disposed within and along said tube, said second fluid conduit having an open proximal end and a closed distal end;
   a second syringe in fluid communication with said second fluid conduit, and
   anchoring means for securely engaging said catheter in a passage, said anchoring means being located on a surface of said balloon and operable by the expansion of said balloon.

2. The catheter according to claim 1, wherein said anchoring means comprises a circumferential rib extending radially outwardly from said balloon.

3. The catheter according to claim 1, wherein said anchoring means comprise a plurality of protrusions extending outwardly from said balloon.

4. The catheter according to claim 1, wherein said anchoring means comprise an external, circumferential, protruding rib extending radially away from said at least one balloon, to engage and to disengage during said at least one balloon's contraction.

5. The catheter of claim 1 wherein said injectable fluid is a radio-opaque material for enabling X-ray visualization of the path of the fistula.

6. A catheter for use within passage, said catheter comprising:
   a tube, said tube having a distal end and a proximal end;
   a balloon in fluid communication with said tube wherein said balloon:
      surrounds a portion of said tube proximally away from said distal end,
      is selectably inflated and outwardly expandable away from said tube, and deflatable and contractible towards said tube; and
      includes anchoring means for the securing of said catheter in said passage, said anchoring means operable by the expansion of said balloon to engage and disengage from said passage during said balloon's contraction;
   an inflating port disposed distally away from said proximal end and attached to said tube;
   an inflating conduit defined by said tube, said conduit being in fluid communication between said balloon and said inflating port;
   a first syringe in fluid communication with said inflating conduit;
   at least one orifice disposed along said tube in said distal section, said at least one orifice forming fluid communication between the outer surface of said tube and the inner surface of said tube;
   a dispensing port attached to said tube;
   a dispensing conduit defined by said tube, said conduit being in fluid communication between said at least one orifice and said dispensing port;
   a second syringe in fluid communication with said dispensing conduit; and
   a wire conduit disposed in said tube, said wire conduit extending between said distal end and said proximal end, said wire conduit being in fluid isolation from said balloon, said orifice and said inflating and dispensing conduits.

7. The catheter according to claim 6, wherein said balloon is formed from a section of said tube.

8. The catheter according to claim 6, wherein said balloon is attached to a section of said tube.

9. The catheter according to claim 6, wherein said balloon includes anchoring means comprising a plurality of protrusions protruding outwardly of said balloon.

10. The catheter according to claim 6, wherein inflation of said balloon activates anchoring means, said anchoring means comprising:
    at least one elongated member having a first end and a second end, wherein:
      said first end is elastically connected to said external tube;
      expansion of said balloon engages said section to said passage;
      contraction of said balloon disengages said member from said passage; and
      a membrane is attached to said tube and to said rods to form sealing means.

11. A catheter according to claim 10, wherein said balloon is attached to a section of said tube and is in fluid communication with said inflating conduit.

12. A catheter according to claim 10, wherein said balloon disposes of engaging means comprising a plurality of protrusions protruding outwardly of said balloon.

13. The catheter according to claim 10, wherein said balloon activates anchoring means, said anchoring means comprising:
    at least one elongated member having a first end and a second end, wherein said first end is elastically connected to said external tube;
    expansion of said balloon engages said section to said passage;
    contraction of said balloon disengages said member from said passage; and
    sealing means formed by a membrane attached to said tube and to said rods.

* * * * *